US009521975B2

(12) United States Patent
Verdooner et al.

(10) Patent No.: US 9,521,975 B2
(45) Date of Patent: Dec. 20, 2016

(54) METHOD FOR DETECTING A DISEASE BY ANALYSIS OF RETINAL VASCULATURE

(71) Applicant: NeuroVision Imaging LLC, Sacramento, CA (US)

(72) Inventors: Steven Verdooner, Sacramento, CA (US); David Biggs, Sacramento, CA (US); Austin Blanco, Sacramento, CA (US)

(73) Assignee: NeuroVision Imaging LLC, Sacramento, CA (US)

( * ) Notice: Subject to any disclaimer, the term of this patent is extended or adjusted under 35 U.S.C. 154(b) by 0 days.

(21) Appl. No.: 14/210,403

(22) Filed: Mar. 13, 2014

(65) Prior Publication Data

US 2014/0268049 A1  Sep. 18, 2014

Related U.S. Application Data

(60) Provisional application No. 61/800,786, filed on Mar. 15, 2013.

(51) Int. Cl.
| | |
|---|---|
| *A61B 3/14* | (2006.01) |
| *A61B 3/10* | (2006.01) |
| *A61B 5/00* | (2006.01) |
| *A61B 3/12* | (2006.01) |

(52) U.S. Cl.
CPC ............. *A61B 5/4088* (2013.01); *A61B 3/102* (2013.01); *A61B 3/1025* (2013.01); *A61B 3/12* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 5,394,199 | A * | 2/1995 | Flower .......................... | 351/206 |
| 7,593,559 | B2 * | 9/2009 | Toth et al. .................... | 382/128 |
| 2009/0244485 | A1 * | 10/2009 | Walsh et al. ........... | A61B 3/102 |
| | | | | 351/221 |

(Continued)

OTHER PUBLICATIONS

Hassenstein Andrea, Clinical use and research applications of Heidelberg retinal angiography and spectraldomain optical coherence tomography—a review, Clinical and Experimental Ophthalmology, 2009, p. 130-143, fig. 12 (http://onlinelibrary.wiley.com/doi/10.1111/j.1442-9071.2009.02017. x/pdf).

(Continued)

*Primary Examiner* — Mohammed Hasan
(74) *Attorney, Agent, or Firm* — Lucas & Mercanti, LLP; Peter J. Phillips

(57) ABSTRACT

A method for detecting a disease such as Alzheimer's disease by analysis of retinal vasculature is disclosed. The method for detecting a disease by analysis of retinal vasculature may include applying a combination of optical retro mode illumination techniques to acquire a plurality of amyloid beta plaques and drusen images that are too small to be seen with other imaging modalities. The disease may also be detected with a non-transitory computer storage media having instructions stored thereon which, when executed, execute the method for detecting a disease by analysis of retinal vasculature. The method may track changes in lumen thickness, plaque, size, area and density of the disease by analysis of retinal vasculature over a predetermined period of time.

18 Claims, 5 Drawing Sheets

(56) References Cited

U.S. PATENT DOCUMENTS

| | | | |
|---|---|---|---|
| 2012/0229766 A1 | 9/2012 | Russmann et al. | |
| 2012/0257164 A1* | 10/2012 | Zee et al. | A61B 3/12 351/206 |
| 2015/0116662 A1* | 4/2015 | Wada | A61B 3/0025 351/206 |

OTHER PUBLICATIONS

Robinson M. Dirk, New Applications of Super-resolution in Medical Imaging, CRC Press, 2010, p. 15-21 (http://people.duke.edu/~sf59/MedicaL_SR_chapter10.pdf).
Jennifer H. Acton, Drusen detection in retro-mode imaging by a scanning laser ophthalmoscope, Acta Ophthalmologica, 2011, 89, p. eA04-e411 (http://onlinelibrary.wiley.com/doi/10.1111/j.1755-3768.2011.02123.x/pdf).

* cited by examiner

METHOD FOR DETECTING A DISEASE BY ANALYSIS OF RETINAL VASCULATURE

This application claims priority to U.S. Provisional Application 61/800,786 filed on Mar. 15, 2013, the entire disclosure of which is incorporated by reference.

BACKGROUND OF THE INVENTION

Field of the Invention

The present invention is a method for detecting. More specifically, the present invention is a method for detecting a disease by analysis of retinal vasculature such as Alzheimer's disease.

Description of the Related Art

The hallmark sign of Alzheimer's disease or AD may be a build-up of amyloid beta plaque in a person's retina. While amyloid may be detected in the brain with amyloid positron emission tomography or PET imaging, the resolution may be relatively low and there must be a meaningful accumulation in order to achieve a positive scan.

In evaluating postmortem retinas, there may be accumulation of amyloid beta plaques in the interior walls of blood vessels resulting in a thinning of the lumen or interior of the blood vessels. From various measurement techniques, it was observed that patients with thinning vessel lumen may be more likely to be at risk for Alzheimer's disease, mild cognitive impairment or MCI or actually have AD. These techniques hold promise as a means of detecting AD prior to symptoms and at relatively early stages as amyloid may build-up to approximately twenty years ahead of the onset of cognitive decline. This may be a basis of a method for determining a level of disease or a risk of obtaining a disease by monitoring changes over a predetermined period of time.

While the method for detecting a disease such as Alzheimer's disease by analysis of retinal vasculature may be performed with traditional fundus cameras, scanning laser ophthalmoscopes with small confocal apertures produce relatively superior results. The utilization of infrared or IR imaging from a scanning laser ophthalmoscope or SLO is relatively more comfortable and advantageous in elderly patients with lens opacities, since light is scattered relatively much less in the presence of media opacities. IR-mode imaging in a confocal scanning laser ophthalmoscope may be utilized to image the retina with an infrared laser. The proposed imaging methods may employ a small confocal aperture to reject light from areas other than the intended focal plane. Vessels may be imaged with the technique and result in sharper edges and reduce scatter.

While the method may be helpful in detection of vessel walls and lumen, the combination of the method with super-resolution and other image processing and analysis techniques may yield a method that may detect changes in a wide variety of vessels, at relatively early stages of disease and also track the changes over a predetermined period of time.

Amyloid beta plaque may be identified in a human brain however identification of the deposits at the relatively earliest stages of disease and of a relatively small size may be impossible with existing retinal imaging technology. This problem may be solved through a combination of IR mode illumination techniques utilizing a confocal laser scanning ophthalmoscope in combination with super-resolution image processing techniques that afford for the imaging of vessel walls and vessel interior lumen that previously were of inadequate quality for measurement with other imaging modalities. Multi-image super-resolution techniques allow recording a series of images and then combining their data set to produce images of relatively extraordinary resolution and image quality thereby resolving the fine details of vessel edges and lumen at relatively early stages of disease. Furthermore, tracking changes in vessel walls and lumen thickness or thinning, size, area, density, reflectivity over time may be likely an indicator of advancing disease and rate of advancing disease. These aspects have never been studied.

BRIEF SUMMARY OF THE INVENTION

The present invention is a method for detecting. More specifically, the present invention is a method for detecting a disease such as Alzheimer's disease by analysis of retinal vasculature.

The method for detecting a disease by analysis of retinal vasculature comprising the steps of imaging a plurality of frames with a plurality of views of a patient user's inner retina layers, aligning and combining the frames utilizing one or more super-resolution techniques, monitoring the aligned and combined frames and quantifying changes in the monitored, aligned and combined frames.

A non-transitory computer storage media having instructions stored thereon which, when executed, execute a method comprising the steps of imaging a plurality of frames of a plurality of views of a patient user's inner retina layers, aligning and combining the frames utilizing one or more super-resolution techniques, monitoring the aligned and combined frames and quantifying changes in the monitored, aligned and combined frames.

It is an object of the present invention to provide a method for detecting a disease by analysis of retinal vasculature optical coherence tomography that is utilized to assess vessel measurements.

It is an object of the present invention to provide a method for detecting a disease by analysis of retinal vasculature where a plurality of fluorescent emission images may be combined with IR mode images to produce a co-located detection matrix.

It is an object of the present invention to provide a method for detecting a disease by analysis of retinal vasculature where a plurality of standard confocal IR images may be combined with retro-mode images to produce a higher sensitivity traditional confocal image or to produce a hyper-contrast combination image.

It is an object of the present invention to provide a method for detecting a disease by analysis of retinal vasculature where an annulus utilized in the IR confocal mode may be replaced with a slit, grid, spinning disk confocal, holographic interference image or coded aperture to further increase detection of traditionally sub-resolvable retinal vessel details.

It is an object of the present invention to provide a method for detecting a disease by analysis of retinal vasculature where a plurality of focal planes may be acquired and combined, to produce a three-dimensional render of a plurality of detected retinal vessels.

It is an object of the present invention to provide a method for detecting a disease by analysis of retinal vasculature where an aperture position may be stepped in the optical path, to alter its interaction with reflected or emitted light from a patient user's retina.

It is an object of the present invention to provide a method for detecting a disease by analysis of retinal vasculature that may be utilized for a variety of imaging procedures including color fundus imaging, fluorescein angiography, ICG angiography, red-free, IR-retro illumination, hyper spectral and multi-spectral imaging and devices that may be utilized in combination with optical coherence tomography.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
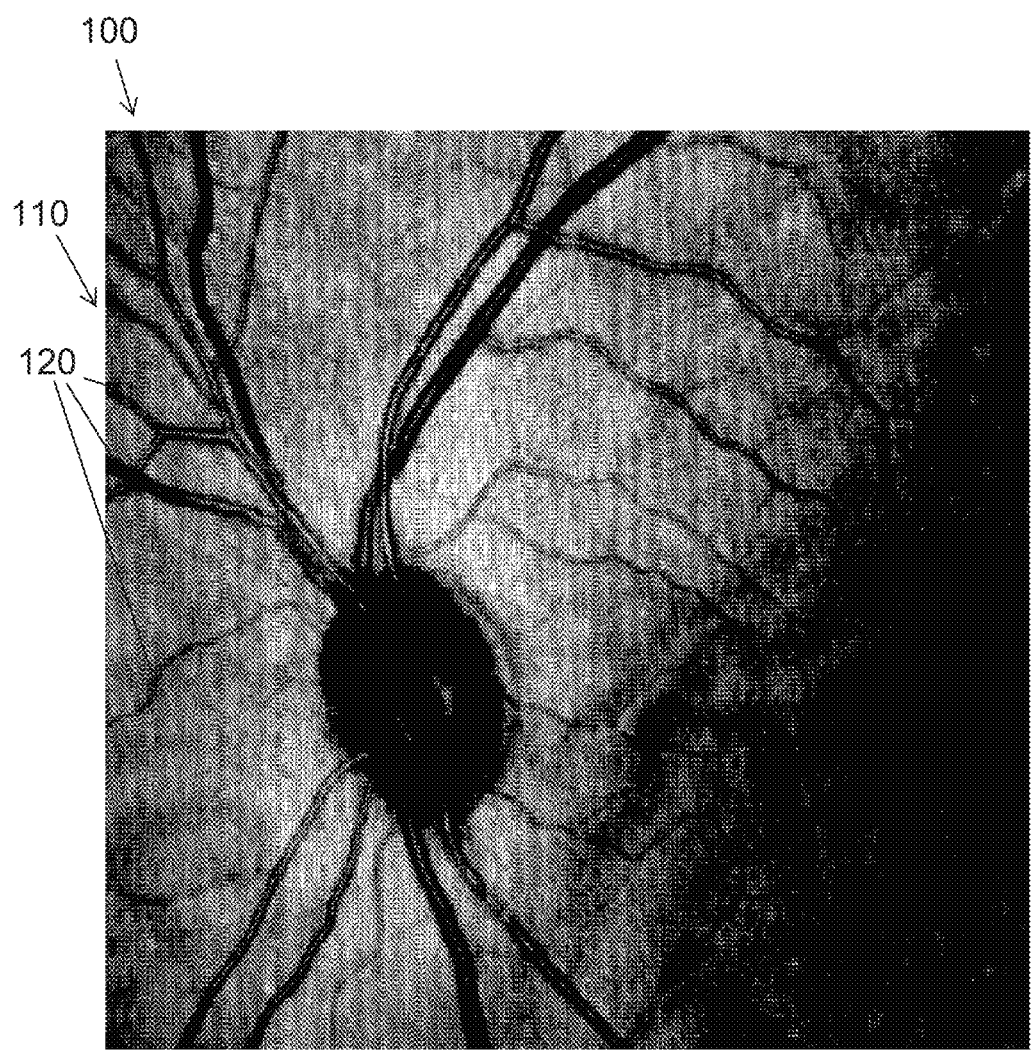
FIG. 1 illustrates a diagram of a first image from a scanning laser ophthalmoscope, in accordance with one embodiment of the present invention.

FIG. 1 illustrates a diagram of a first image 100 from a scanning laser ophthalmoscope, in accordance with one embodiment of the present invention.

As illustrated in FIG. 1, the first image 100 may be a patient user's inner retina layers 110. More specifically, the first image 100 may be one or more vessel measurements 120. The first image 100 may be generated by a scanning laser ophthalmoscope without utilizing one or more super-resolution techniques.

Figure 2:
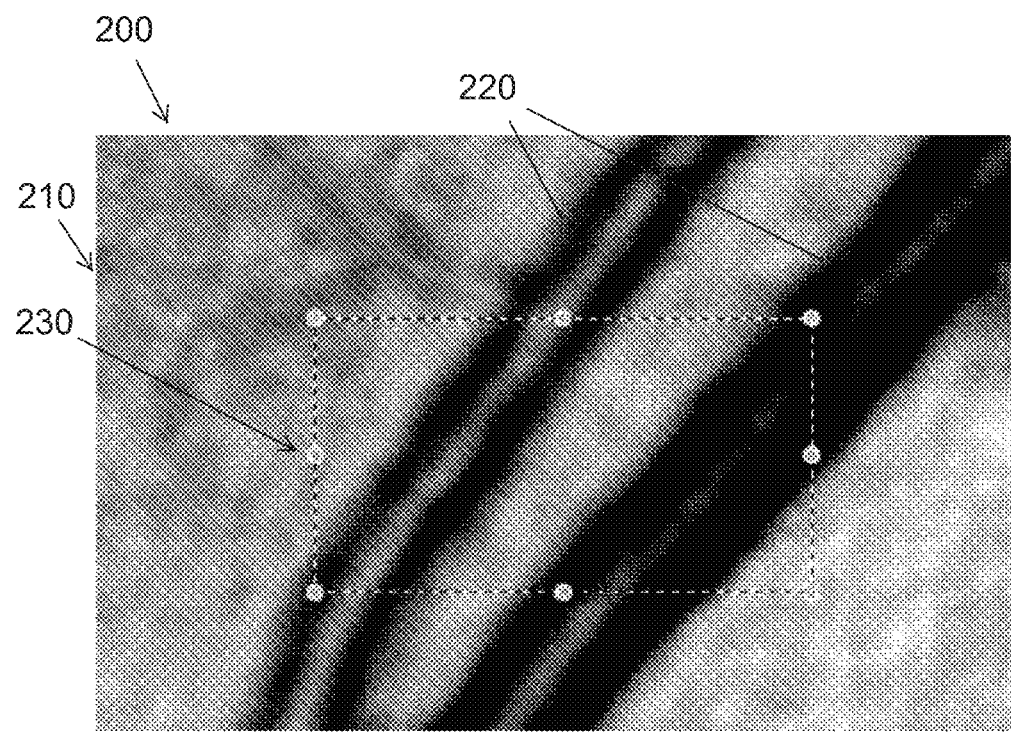
FIG. 2 illustrates a diagram of a second image from a scanning laser ophthalmoscope utilizing one or more super-resolution techniques, in accordance with one embodiment of the present invention.

FIG. 2 illustrates a diagram of a second image 200 from a scanning laser ophthalmoscope utilizing one or more super-resolution techniques, in accordance with one embodiment of the present invention.

As illustrated in FIG. 2, the second image 200 may be a patient user's inner retina layers 210. More specifically, the second image 200 may be a plurality of vessel measurements 220. The second image 200 may be a combined plurality of vessel measurements 230 generated by a scanning laser ophthalmoscope utilizing one or more super-resolution techniques.

Figure 3:
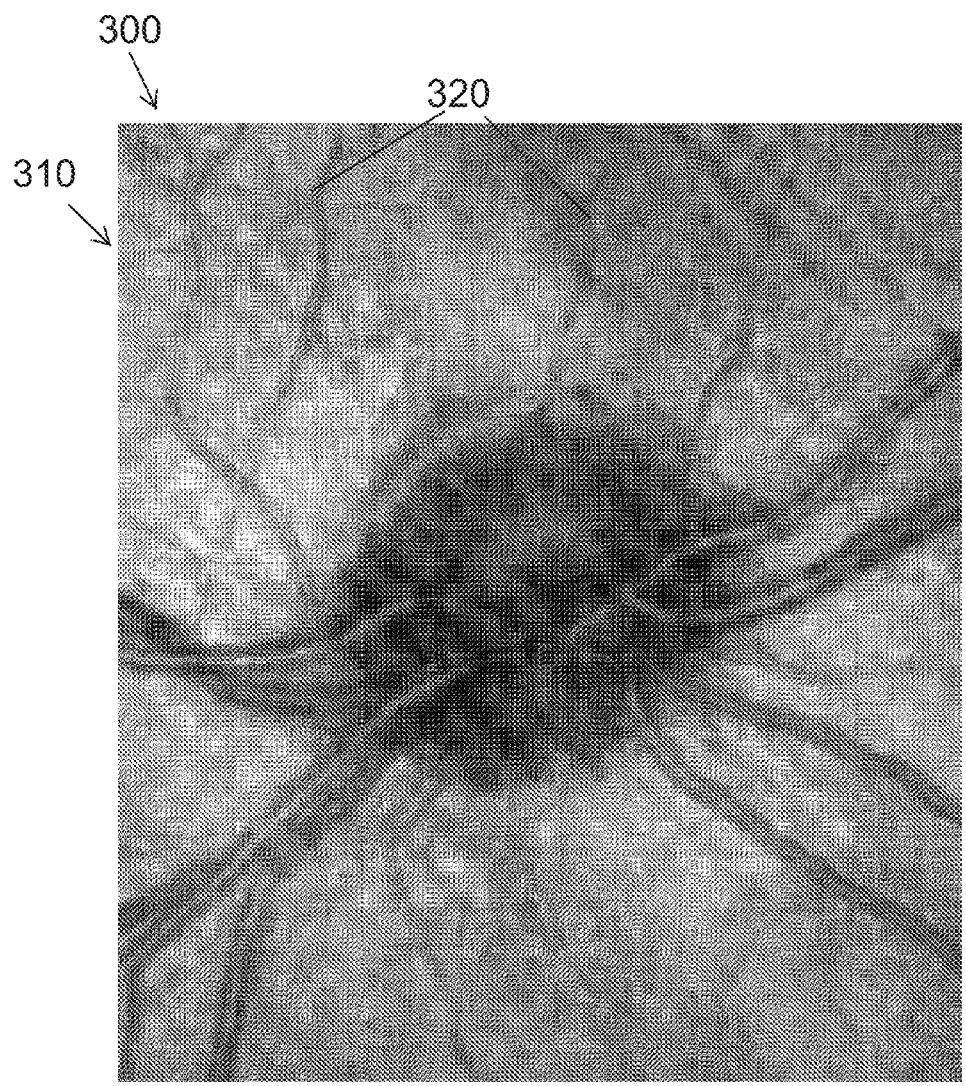
FIG. 3 illustrates a diagram of a third image from a scanning laser ophthalmoscope utilizing one or more super-resolution techniques, in accordance with one embodiment of the present invention.

FIG. 3 illustrates a diagram of a third image 300 from a scanning laser ophthalmoscope utilizing one or more super-resolution techniques, in accordance with one embodiment of the present invention.

As illustrated in FIG. 3, the third image 300 may be a patient user's inner retina layers 310. More specifically, the third image 300 may be a plurality of vessel measurements 320. The vessel measurements 320 may be generated by a scanning laser ophthalmoscope utilizing one or more super-resolution techniques.

Figure 4:
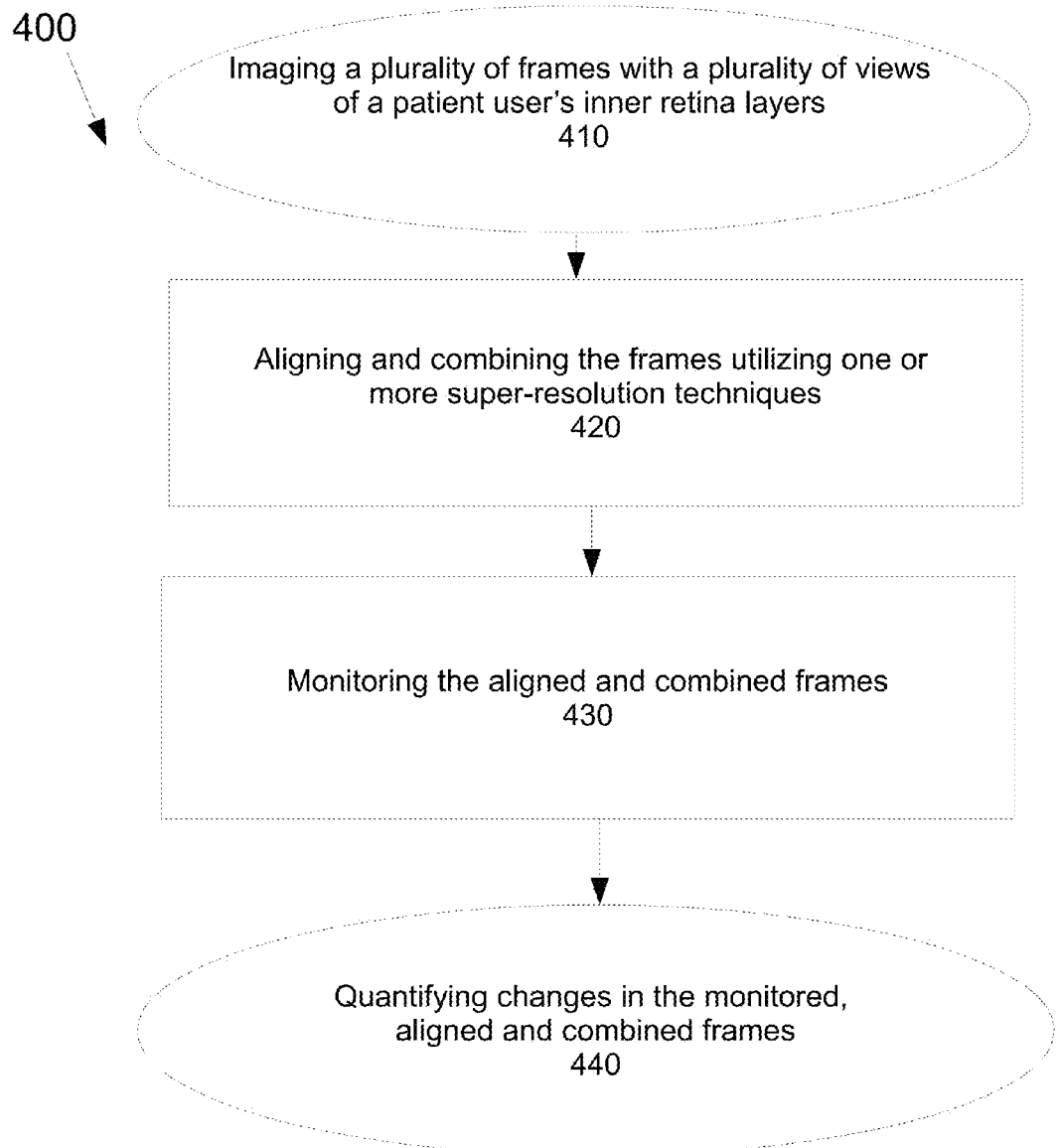
FIG. 4 illustrates a flowchart of a method for detecting a disease by analysis of retinal vasculature, in accordance with one embodiment of the present invention.

FIG. 4 illustrates a flowchart of a method 400 for detecting a disease by analysis of retinal vasculature, in accordance with one embodiment of the present invention.

The method 400 may include the steps of imaging a plurality of frames with a plurality of views of a patient user's inner retina layers 410, aligning and combining the frames utilizing one or more super-resolution techniques 420, monitoring the aligned and combined frames 430 and quantifying changes in the monitored, aligned and combined frames 440.

The imaging step 410 may include utilizing optical coherence tomography to assess one or more vessel measurements. The aligning and combining step 420 may include the one or more super-resolution techniques that may be selected from the group consisting of color fundus imaging, fluorescein angiography, Indocyanine Green or ICG angiography, red-free illumination, IR-retro illumination, hyper spectral imaging or multi-spectral imaging. The aligning and combining step 420 may include a plurality of standard confocal IR images that may be combined with retro-mode images to produce a higher sensitivity traditional confocal image or to produce a hyper-contrast combination image. The aligning and combining step 420 may include a plurality of standard confocal IR images that may be combined with retro-mode images to produce a higher sensitivity traditional confocal image or to produce a hyper-contrast combination image. The aligning and combining step 420 may include an annulus utilized in an IR confocal mode that may be replaced with a slit, grid, spinning disk confocal, holographic interference image or coded aperture to further increase detection of traditionally sub-resolvable retinal vessel details. The aligning and combining step 420 may include a plurality of focal planes that may be acquired and combined, to produce a three-dimensional render of a plurality of detected retinal vessels. The aligning and combining step 420 may include an aperture position that may be stepped in an optical path, to alter its interaction with reflected or emitted light from the patient user's retina. The monitoring step 430 may be performed by a non-transitory storage media, a processor and a memory system. The quantifying step 440 may be performed by a non-transitory storage media, a processor and a memory system. The quantifying step 440 may include a plurality of fluorescent emission images that may be combined with a plurality of IR mode images to produce a co-located detection matrix. The method 400 may treat a disease that is Alzheimer's disease.

Figure 5:
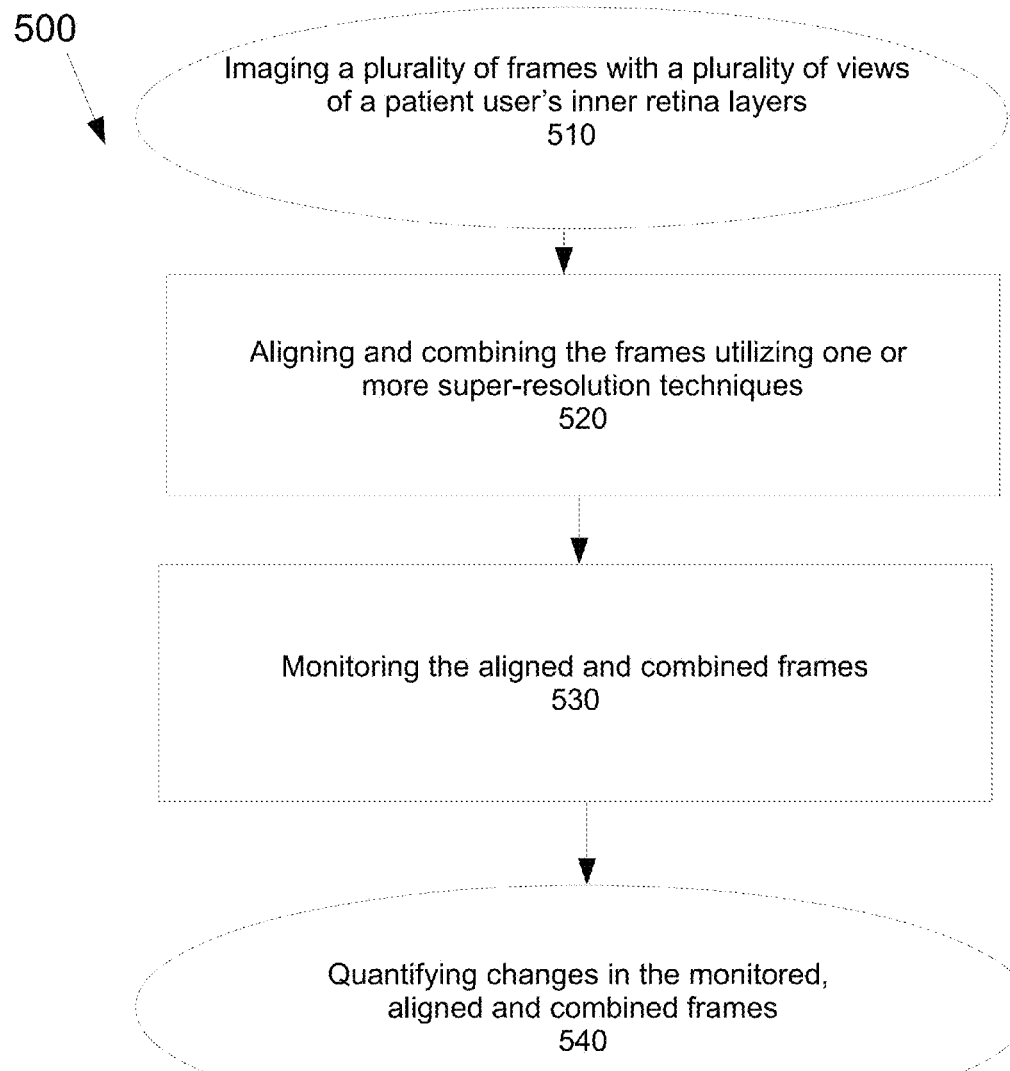
FIG. 5 illustrates a flowchart of a method for detecting a disease by analysis of retinal vasculature by a non-transitory computer storage media having instructions stored thereon which, when executed, execute the method, in accordance with one embodiment of the present invention.

FIG. 5 illustrates a flowchart of a method for detecting a disease by analysis of retinal vasculature by a non-transitory computer storage media 500 having instructions stored thereon which, when executed, execute the method, in accordance with one embodiment of the present invention.

The non-transitory computer storage media 500 may execute the method steps of imaging a plurality of frames with a plurality of views of a patient user's inner retina layers 510, aligning and combining the frames utilizing one or more super-resolution techniques 520, monitoring the aligned and combined frames 530 and quantifying changes in the monitored, aligned and combined frames 540.

The imaging step 510 may include utilizing optical coherence tomography to assess one or more vessel measurements. The aligning and combining step 520 may include the one or more super-resolution techniques that may be selected from the group consisting of color fundus imaging, fluorescein angiography, Indocyanine Green or ICG angiography, red-free illumination, IR-retro illumination, hyper spectral imaging or multi-spectral imaging. The aligning and combining step 520 may include a plurality of standard confocal IR images that may be combined with retro-mode images to produce a higher sensitivity traditional confocal image or to produce a hyper-contrast combination image. The aligning and combining step 520 may include a plurality of standard confocal IR images that may be combined with retro-mode images to produce a higher sensitivity traditional confocal image or to produce a hyper-contrast combination image. The aligning and combining step 520 may include an annulus utilized in an IR confocal mode that may be replaced with a slit, grid, spinning disk confocal, holographic interference image or coded aperture to further increase detection of traditionally sub-resolvable retinal vessel details. The aligning and combining step 520 may include a plurality of focal planes are acquired and combined, to produce a three-dimensional render of a plurality of detected retinal vessels. The aligning and combining step 520 may include an aperture position that may be stepped in an optical path, to alter its interaction with reflected or emitted light from the patient user's retina. The monitoring step 530 may be performed by a non-transitory storage media, a processor and a memory system. The quantifying step 540 may be performed by a non-transitory storage media, a processor and a memory system. The quantifying step 540 may include a plurality of fluorescent emission images that may be combined with a plurality of IR mode images to produce a co-located detection matrix. The non-transitory computer storage media 500 may treat a disease that is Alzheimer's disease.

Multiple images may be acquired utilizing a variety of imaging modalities and from a variety of retinal imaging devices including fundus cameras and scanning laser ophthalmoscopes or SLOs. Infrared images from a SLO may utilize a small confocal aperture to give the best results. These images may be transferred to a software program or non-transitory storage media which accomplishes several tasks.

The software program or non-transitory storage media may co-register each of the images. The non-transitory storage media may increase contrast where intensity shifts from one image interact with intensity shifts in another image. This technique may increase a signal by subtracting noise. Subtraction may be accomplished by referencing the numerous modal images and producing a result where the noise or artifact error from each type of retro mode, may be removed, leaving only the combined signal structures from each IR mode image. This super resolution image may be relatively highly improved over each individual retro mode image and by reducing the signal and building the noise in this image, relatively higher detection sensitivity may be achieved in the final image.

Utilizing the previous step, a high bit depth approximately greater than an eight bit final image may be produced which may be analyzed utilizing conventional methods. This may result in a plurality of images with vessel edges and vessel lumen that may be relatively easily discernable.

The method for detecting a disease such as Alzheimer's disease by analysis of retinal vasculature may be utilized for detection and advancement of Alzheimer's disease research. Multiple frames of a plurality of views of the retinal vasculature may be imaged, both peripherally and also at relatively high magnification, aligning and combining frames utilizing super-resolution techniques. The changes to the multiple frames may be quantified and tracked over a predetermined period of time such as a day, a week, a month or a year.

While the present invention has been related in terms of the foregoing embodiments, those skilled in the art will recognize that the invention is not limited to the embodiments described. The present invention may be practiced with modification and alteration within the spirit and scope of the appended claims. Thus, the description is to be regarded as illustrative instead of restrictive on the present invention.

The invention claimed is:

1. A method for detecting a disease by analysis of retinal vasculature, comprising the steps of:
   imaging a plurality of frames with a plurality of views of a patient user's inner retina layers, wherein the imaging utilizes optical coherence tomography to assess one or more vessel measurements;
   aligning and combining the frames utilizing one or more super-resolution techniques;
   monitoring the aligned and combined frames; and
   quantifying changes in the monitored, aligned and combined frames.

2. The method according to claim 1, wherein the aligning and combining includes the one or more super-resolution techniques that are selected from the group consisting of color fundus imaging, fluorescein angiography, ICG angiography, red-free illumination, IR-retro illumination, hyper spectral imaging or multi-spectral imaging.

3. The method according to claim 1, wherein the aligning and combining includes a plurality of standard confocal IR images that are combined with a plurality of retro-mode images to produce a higher sensitivity traditional confocal image or to produce a hyper-contrast combination image.

4. The method according to claim 1, wherein the aligning and combining includes an annulus utilized in an IR confocal mode that is replaced with a slit, grid, spinning disk confocal, holographic interference image or a coded aperture to further increase detection of traditionally sub-resolvable retinal vessel details.

5. The method according to claim 1, wherein the aligning and combining includes a plurality of focal planes that are acquired and combined, to produce a three-dimensional render of a plurality of detected retinal vessels.

6. The method according to claim 1, wherein the aligning and combining includes an aperture position is stepped in an optical path, to alter its interaction with reflected or emitted light from the patient user's retina.

7. The method according to claim 1, wherein the monitoring and the quantifying is performed by a non-transitory storage media, a processor and a memory system.

8. The method according to claim 1, wherein the quantifying includes a plurality of fluorescent emission images that are combined with a plurality of IR mode images to produce a co-located detection matrix.

9. The method according to claim 1, wherein the disease is Alzheimer's disease.

10. A non-transitory computer storage media having instructions stored thereon which, when executed, execute a method comprising the steps of:
    imaging a plurality of frames of a plurality of views of a patient user's inner retina layers, wherein the imaging utilizes optical coherence tomography to assess one or more vessel measurements;
    aligning and combining the frames utilizing one or more super-resolution techniques;
    monitoring the aligned and combined frames; and
    quantifying changes in the monitored, aligned and combined frames.

11. The method according to claim 10, wherein the aligning and combining includes the one or more super-resolution techniques that are selected from the group consisting of color fundus imaging, fluorescein angiography, ICG angiography, red-free illumination, IR-retro illumination, hyper spectral imaging or multi-spectral imaging.

12. The method according to claim 10, wherein the aligning and combining includes a plurality of standard confocal IR images that are combined with a plurality of retro-mode images to produce a higher sensitivity traditional confocal image or to produce a hyper-contrast combination image.

13. The method according to claim 10, wherein the aligning and combining includes an annulus utilized in an IR confocal mode that is replaced with a slit, grid, spinning disk confocal, holographic interference image or a coded aperture to further increase detection of traditionally sub-resolvable retinal vessel details.

14. The method according to claim 10, wherein the aligning and combining includes a plurality of focal planes that are acquired and combined, to produce a three-dimensional render of a plurality of detected retinal vessels.

15. The method according to claim 10, wherein the aligning and combining includes an aperture position is stepped in an optical path, to alter its interaction with reflected or emitted light from the patient user's retina.

16. The method according to claim 10, wherein the monitoring and the quantifying is performed by a non-transitory storage media, a processor and a memory system.

17. The method according to claim 10, wherein the quantifying includes a plurality of fluorescent emission images that are combined with a plurality of IR mode images to produce a co-located detection matrix.

18. The method according to claim 10, wherein the disease is Alzheimer's disease.

* * * * *